US008029550B2

(12) United States Patent
Dewey et al.

(10) Patent No.: US 8,029,550 B2
(45) Date of Patent: Oct. 4, 2011

(54) INTERVERTEBRAL PROSTHETIC DEVICE FOR SPINAL STABILIZATION AND METHOD OF IMPLANTING SAME

(75) Inventors: Jonathan M. Dewey, Raleigh, NC (US); Fred J. Molz, IV, Birmingham, AL (US); Aurelien Bruneau, Jacksonville, FL (US); Eric C. Lange, Pleasanton, CA (US); Matthew M. Morrison, Cordova, TN (US); Thomas A. Carls, Memphis, TN (US); Kent M. Anderson, Sunnyvale, CA (US); Jean M. Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 184 days.

(21) Appl. No.: 12/573,779

(22) Filed: Oct. 5, 2009

(65) Prior Publication Data
US 2010/0030285 A1    Feb. 4, 2010

Related U.S. Application Data

(62) Division of application No. 11/333,919, filed on Jan. 18, 2006, now abandoned.

(51) Int. Cl.
*A61B 17/88* (2006.01)
*A61B 17/70* (2006.01)
(52) U.S. Cl. .................. 606/279; 606/248; 606/249
(58) Field of Classification Search .................. 606/279, 606/60, 246, 248, 249
See application file for complete search history.

(56) References Cited

U.S. PATENT DOCUMENTS

| 2,077,804 A | 4/1937 | Morrison |
| 2,677,369 A | 5/1954 | Knowles |
| 3,648,691 A | 3/1972 | Lumb et al. |
| 4,011,602 A | 3/1977 | Rybicki et al. |
| 4,257,409 A | 3/1981 | Bacal et al. |
| 4,554,914 A | 11/1985 | Kapp et al. |
| 4,573,454 A | 3/1986 | Hoffman |
| 4,604,995 A | 8/1986 | Stephens et al. |

(Continued)

FOREIGN PATENT DOCUMENTS
DE    2821678 A1    11/1979
(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — Ellen C Hammond (57) ABSTRACT

A method of implanting a spinal prosthesis comprises inserting a first member between superior and inferior spinous processes associated with respective superior and inferior vertebrae. The superior and inferior vertebrae are separated by an intermediate vertebra. The method further includes inserting a second member through a channel in the first member. After the second member is inserted, the method requires removing the second member from the channel and inserting a third member through the channel. The third member has a different stiffness than the second member. Finally, the method requires anchoring the third member to the intermediate vertebra, while the third member is inserted through the channel. The third member is anchored at first and second locations disposed on respective first and second lateral sides of the intermediate vertebra.

14 Claims, 4 Drawing Sheets

U.S. PATENT DOCUMENTS

| | | |
|---|---|---|
| 4,632,101 A | 12/1986 | Freedland |
| 4,657,550 A | 4/1987 | Daher |
| 4,686,970 A | 8/1987 | Dove et al. |
| 4,696,887 A | 9/1987 | Sato et al. |
| 4,827,918 A | 5/1989 | Olerud |
| 4,863,476 A | 9/1989 | Shepperd |
| 4,931,055 A | 6/1990 | Bumpus et al. |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,306,275 A | 4/1994 | Bryan |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,415,661 A | 5/1995 | Holmes |
| 5,437,672 A | 8/1995 | Alleyne |
| 5,454,812 A | 10/1995 | Lin |
| 5,496,318 A | 3/1996 | Howland et al. |
| 5,518,498 A | 5/1996 | Lindenberg et al. |
| 5,554,191 A | 9/1996 | Lahille et al. |
| 5,609,634 A | 3/1997 | Voydeville |
| 5,609,635 A | 3/1997 | Michelson |
| 5,628,756 A | 5/1997 | Barker, Jr. et al. |
| 5,645,599 A | 7/1997 | Samani |
| 5,665,122 A | 9/1997 | Kambin |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,746,762 A | 5/1998 | Bass |
| 5,755,797 A | 5/1998 | Baumgartner |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,113,639 A | 9/2000 | Ray et al. |
| 6,126,689 A | 10/2000 | Brett |
| 6,127,597 A | 10/2000 | Beyar et al. |
| 6,132,464 A | 10/2000 | Martin |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,758,863 B2 | 7/2004 | Estes et al. |
| 6,761,720 B1 | 7/2004 | Senegas |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 2002/0143331 A1 | 10/2002 | Zucherman et al. |
| 2003/0153915 A1 | 8/2003 | Nekozuka et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0151116 A1 | 7/2007 | Malandain |
| 2007/0162000 A1 | 7/2007 | Perkins |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2007/0276493 A1 | 11/2007 | Malandain et al. |
| 2007/0282443 A1 | 12/2007 | Globerman et al. |
| 2008/0058934 A1 | 3/2008 | Malandain et al. |
| 2008/0161818 A1 | 7/2008 | Kloss et al. |
| 2008/0262617 A1 | 10/2008 | Froehlich et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| WO | 94/26192 | 11/1994 |
| WO | 94/26195 | 11/1994 |
| WO | 98/20939 | 5/1998 |
| WO | 99/26562 | 6/1999 |
| WO | 00/44319 | 8/2000 |
| WO | 01/54598 A1 | 8/2001 |
| WO | 03/057055 A1 | 7/2003 |
| WO | 2004/047689 A1 | 6/2004 |
| WO | 2004/047691 A1 | 6/2004 |
| WO | 2004/084768 A2 | 10/2004 |
| WO | 2005/009300 A1 | 2/2005 |
| WO | 2005/011507 A1 | 2/2005 |
| WO | 2005/044118 A1 | 5/2005 |
| WO | 2005/048856 A1 | 6/2005 |
| WO | 2005/110258 A1 | 11/2005 |
| WO | 2006/064356 A1 | 6/2006 |
| WO | 2007/034516 A1 | 3/2007 |
| WO | 2007052975 A1 | 5/2007 |

OTHER PUBLICATIONS

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Aota et al., "Postfusion Instability at the Adjacent Segments After Rigid Pedicle Screw Fixation for Degenerative Lumbar Spinal Disorders," J. Spinal Dis., Dec. 1995, pp. 464-473, vol. 8, No. 6.

Benzel et al., "Posterior Cervical Interspinous Compression Wiring and Fusion for Mid to Low Cervical Spinal Injuries," J. Neurosurg., Jun. 1989, pp. 893-899, vol. 70.

Booth et al., "Complications and Predictive Factors for the Successful Treatment of Flatback Deformity (Fixed Sagittal Imbalance)," SPINE, 1999, pp. 1712-1720, vol. 24, No. 16.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müuller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rahm et al., "Adjacent-Segment Degeneration After Lumbar Fusion with Instrumentation: A Retrospective Study," J. Spinal Dis., Oct. 1996, pp. 392-400, vol. 9, No. 5.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schären et al, "Erfolge und Probleme langstreckiger Fusionen der degenerativen Lendenwirbelsäule," Osteosynthese International, Jul. 17, 1998, pp. 173-179, vol. 6, Johann Ambrosius Barth.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "Lumbar Motion Segment Pathology Adjacent to Thoracolumbar, Lumbar, and Lumbosacral Fusions," SPINE, Apr. 15, 1996, pp. 970-981, vol. 21, No. 8.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

INTERVERTEBRAL PROSTHETIC DEVICE FOR SPINAL STABILIZATION AND METHOD OF IMPLANTING SAME

This application is a divisional of application Ser. No. 11/333,919, filed Jan. 18, 2006, now abandoned, the disclosure of which is incorporated herein by reference.

BACKGROUND

The present invention relates to an intervertebral prosthetic device for stabilizing the human spine, and a method of implanting same.

Spinal discs that extend between adjacent vertebrae in vertebral columns of the human body provide critical support between the adjacent vertebrae while permitting multiple degrees of motion.

These discs can rupture, degenerate, and/or protrude by injury, degradation, disease, or the like to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column and are supported by the respective spinous processes of the vertebrae to prevent the collapse of the intervertebral space between the adjacent vertebrae and provide motion stabilization of the spine. Many of these devices are supported between the spinous processes of the adjacent vertebrae.

In some situations it is often necessary to remove the laminae and the spinous process from at least one of the adjacent vertebrae to get proper decompression. In other situations, the defective disc is removed and two vertebral segments are fused together to stop any motion between the segments and thus relieve the pain. When two adjacent vertebrae are fused, the laminae and the spinous process of at least one vertebra are no longer needed and are therefore often removed.

However, in both of the above situations involving removal of a spinous process, it would be impossible to implant an intervertebral prosthetic device of the above type since the device requires support from both processes.

SUMMARY

According to an embodiment of the invention, an intervertebral prosthetic device is provided that is implantable between two adjacent vertebrae, at least one of which is void of a spinous process, to provide motion stabilization.

Various embodiments of the invention may possess one or more of the above features and advantages, or provide one or more solutions to the above problems existing in the prior art.

DETAILED DESCRIPTION

Figure 1:
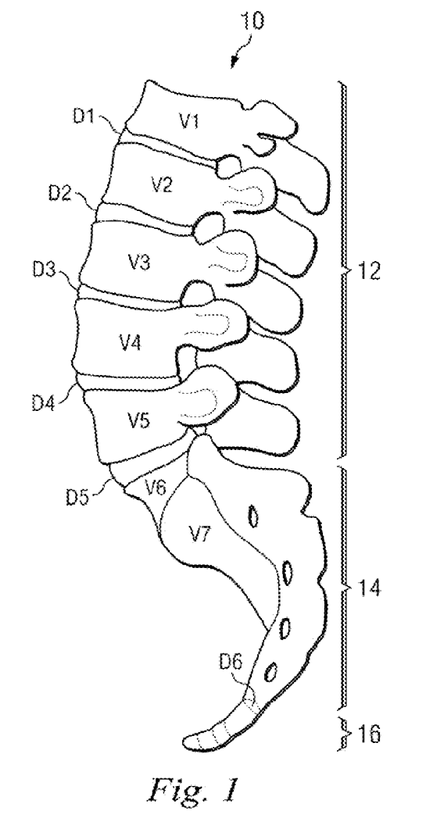
FIG. 1 is a side elevational view of an adult human vertebral column.
Figure 2:
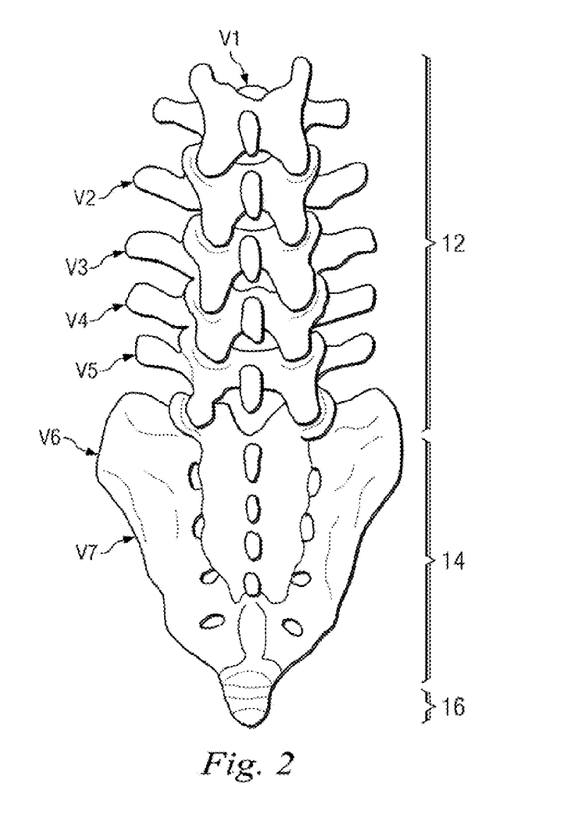
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the sacrum 14, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The vertebra V6 includes five fused vertebrae, one of which is a superior sacrum 14 separated from the vertebra V5 by a disc D5. The other four fused vertebrae of the sacrum 14 are referred to collectively as V7. A disc D6 separates the vertebra V6 from the coccyx 16 which includes four fused vertebrae (not referenced).

Figures 3, 4:
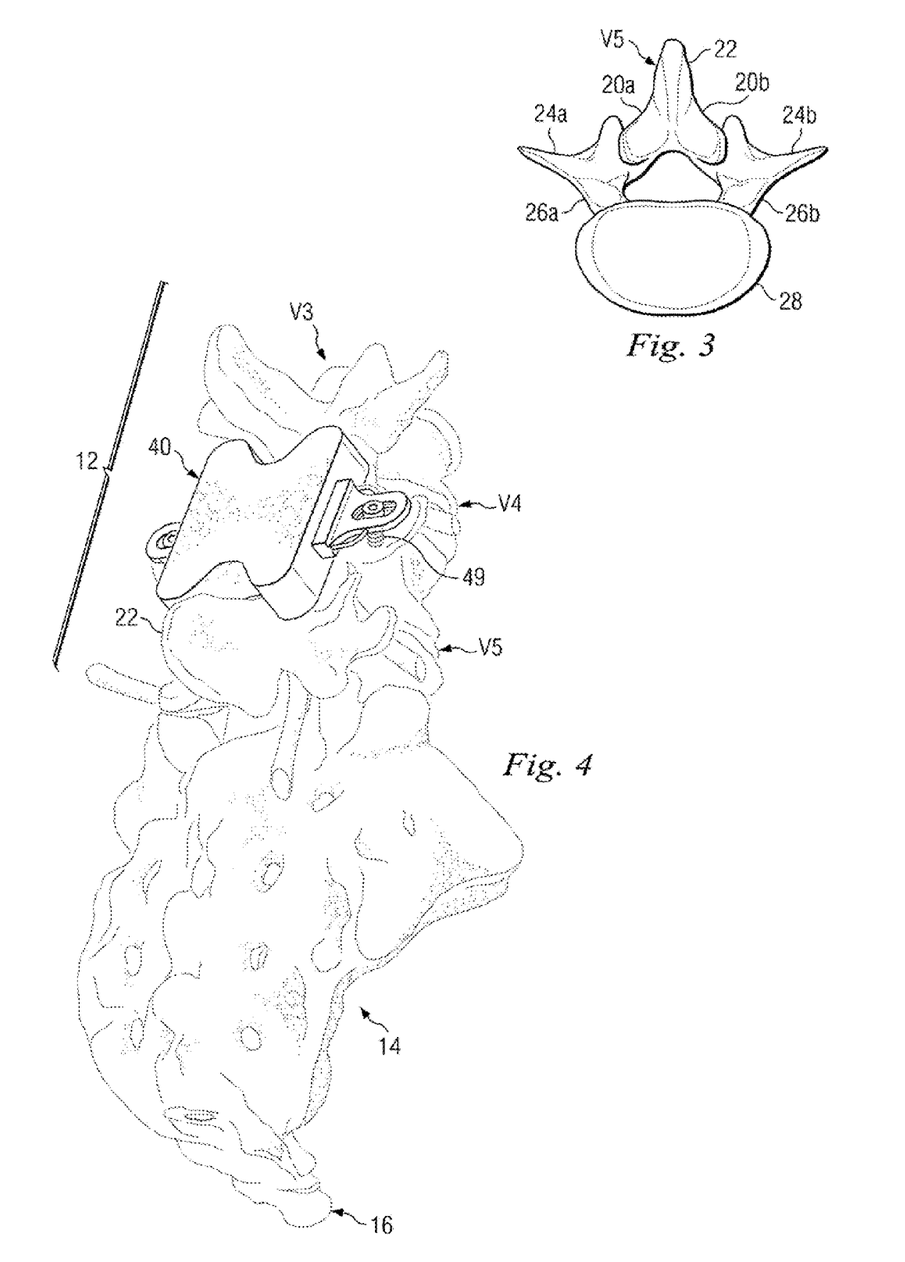
FIG. 3 is an enlarged, front elevational view of one of the vertebrae of the column of FIGS. 1 and 2.
FIG. 4 is an enlarged, partial, isometric view of a portion of the column of FIGS. 1 and 2, including the lower three vertebrae of the column, and depicting an intervertebral prosthetic device according to an embodiment of the invention implanted between two adjacent vertebrae.

With reference to FIG. 3, the vertebra V5 includes two laminae 20a and 20b extending to either side (as viewed in FIG. 2) of a spinous process 22 that projects posteriorly from the juncture of the two laminae. Two transverse processes 24a and 24b extend laterally from the laminae 20a and 20b, respectively, and two pedicles 26a and 26b extend inferiorly from the processes 24a and 24b to a vertebral body 28. Since the other vertebrae V1-V3 are similar to the vertebra V5 they will not be described in detail. Also, V4 is similar to V5 with the exception that the spinous process 22 of V4 has been removed for one or both of the reasons set forth below.

Referring to FIG. 4, it will be assumed that, for one or more of the reasons set forth above, the vertebrae V4 and V5 are not being adequately supported by the disc D4 and that it is therefore necessary to provide supplemental support and stabilization of these vertebrae. As stated above, it will also be assumed that the spinous process 22 of V4 has been removed.

An intervertebral disc prosthetic device 40 according to an embodiment of the invention is provided which is adapted to be implanted between the spinous processes 22 of the vertebrae V3 and V5. The prosthetic device 40 is shown in detail in FIGS. 5 and 6 and includes a spacer 42 which is substantially rectangular in shape with the exception that two curved notches 42a and 42b are formed in the respective end portions thereof. A laterally extending channel 42c, having a substantially rectangular cross section, extends through the entire width of the spacer 42 approximately midway between the notches 42a and 42b.

Figures 5, 6:
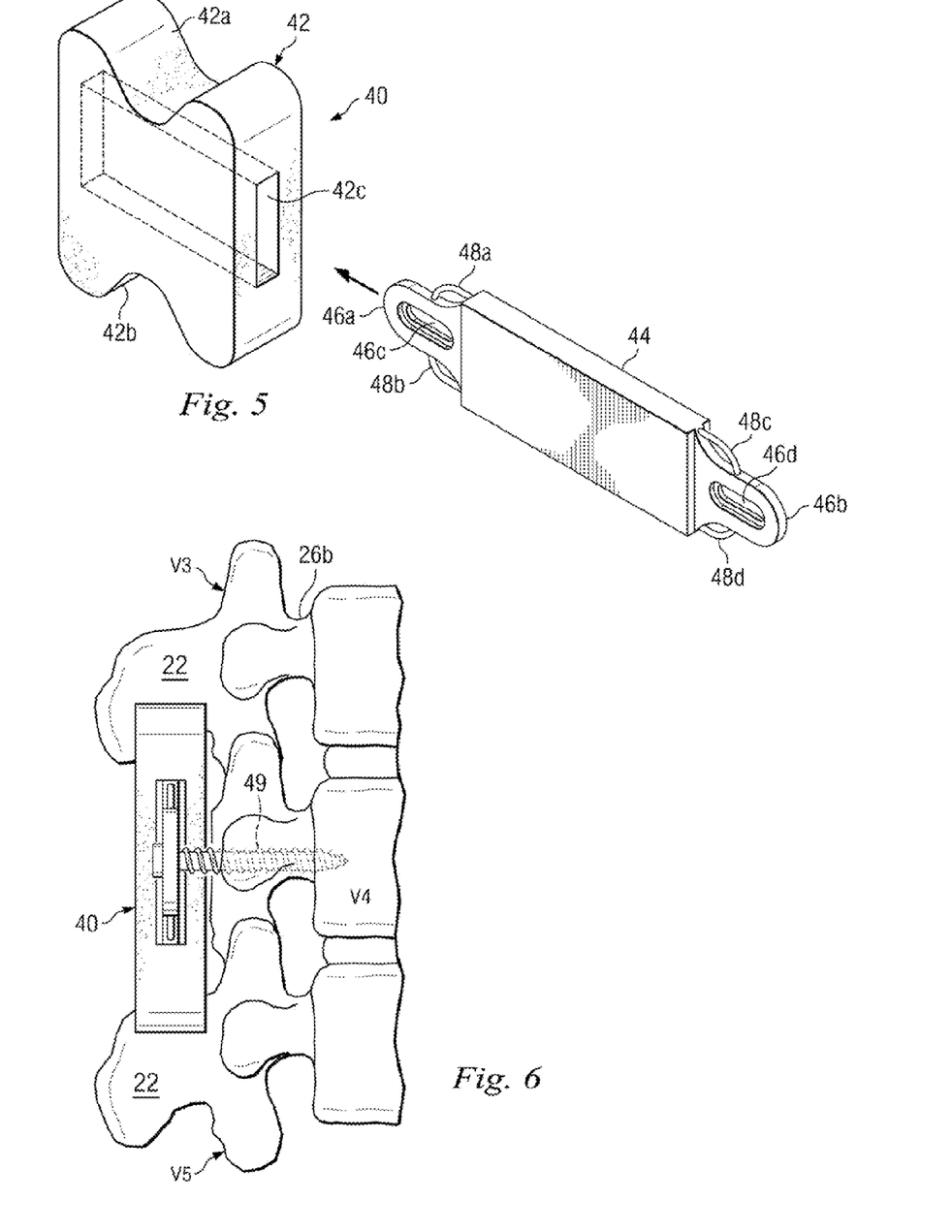
FIG. 5 is an enlarged, isometric, exploded view of the prosthetic device of FIG. 4.
FIG. 6 is a cross-sectional view of the implanted device of FIGS. 4 and 5.

An insert 44 is provided that is dimensioned so as to extend in the channel 42c with minimum clearance. Tabs 46a and 46b extend out from the respective ends of the insert 44 and elongated openings 46c and 46d extend through the respective tabs. The length of the insert 44 substantially corresponds to the length of the channel 42c so that when the insert is inserted in the channel, the tabs 46a and 46b project outwardly from the channel.

Two protrusions 48a and 48b extend from the sides of the tab 46a and two protrusions 48c and 48d extend from the sides of the tab 46b. The protrusions are for the purpose of receiving tethers, or the like, to tether the device 40 to the vertebrae V4 and/or V5.

Since the spinous process of the vertebra V4 has been removed, the device 40 is implanted between the spinous process 22 of the vertebra V3 and the spinous process 22 of the vertebra V5. In the implanted position shown in FIGS. 4 and 6, the spinous process 22 of the vertebra V3 extends in the notch 42a of the spacer 42, and the spinous process 22 of the vertebra V5 extends in the notch 42b. The dimensions of the device 40 are such that, when it is implanted in this manner, the elongated openings 46c and 46d extend over the pedicles 26a and 26b (FIG. 3) of the vertebra V4.

Then, two screws, one of which is referred to by the reference numeral 49 in FIGS. 4 and 6, are inserted through the elongated openings 42c and 42d, respectively, of the spacer 42. Torque is applied to the screws 49 so that they are driven into the pedicles 26a and 26b of the vertebra V4. The elongated openings 46c and 46d in the tabs 46a and 46b, respectively, enable the screws 49 to be adjusted laterally and to be angled towards the pedicles 26a and 26b as necessary so that they can be driven into the pedicles.

Although not shown in the drawing, tethers can be tied between the protrusions 48a-48d and the vertebrae V3, V4, and/or V5 to provide additional support and resistance.

As examples of the materials making up the spacer 42 and the insert 44, the spacer can be of a relatively soft material, such as soft plastic, including silicone, while the insert can be of a relatively stiff material, such as hard plastic or rubber. In the latter context, the surgeon could be provided with several inserts 44 that vary in stiffness, and once the condition of the vertebrae V4 and V5 (FIG. 4), and therefore the desired stiffness, is determined, the proper insert 44 can be selected.

When the device 40 is implanted in the manner discussed above, the relatively flexible, soft spacer 42 provides non-rigid connections to the vertebrae V3 and V5 that readily conforms to the spinous processes 22 of the vertebrae V3 and V5 and provides excellent shock absorption, while the insert 44 adds stiffness, compressive strength and durability, and the screws 49 provide a rigid connection to the vertebra V4.

Figure 7:
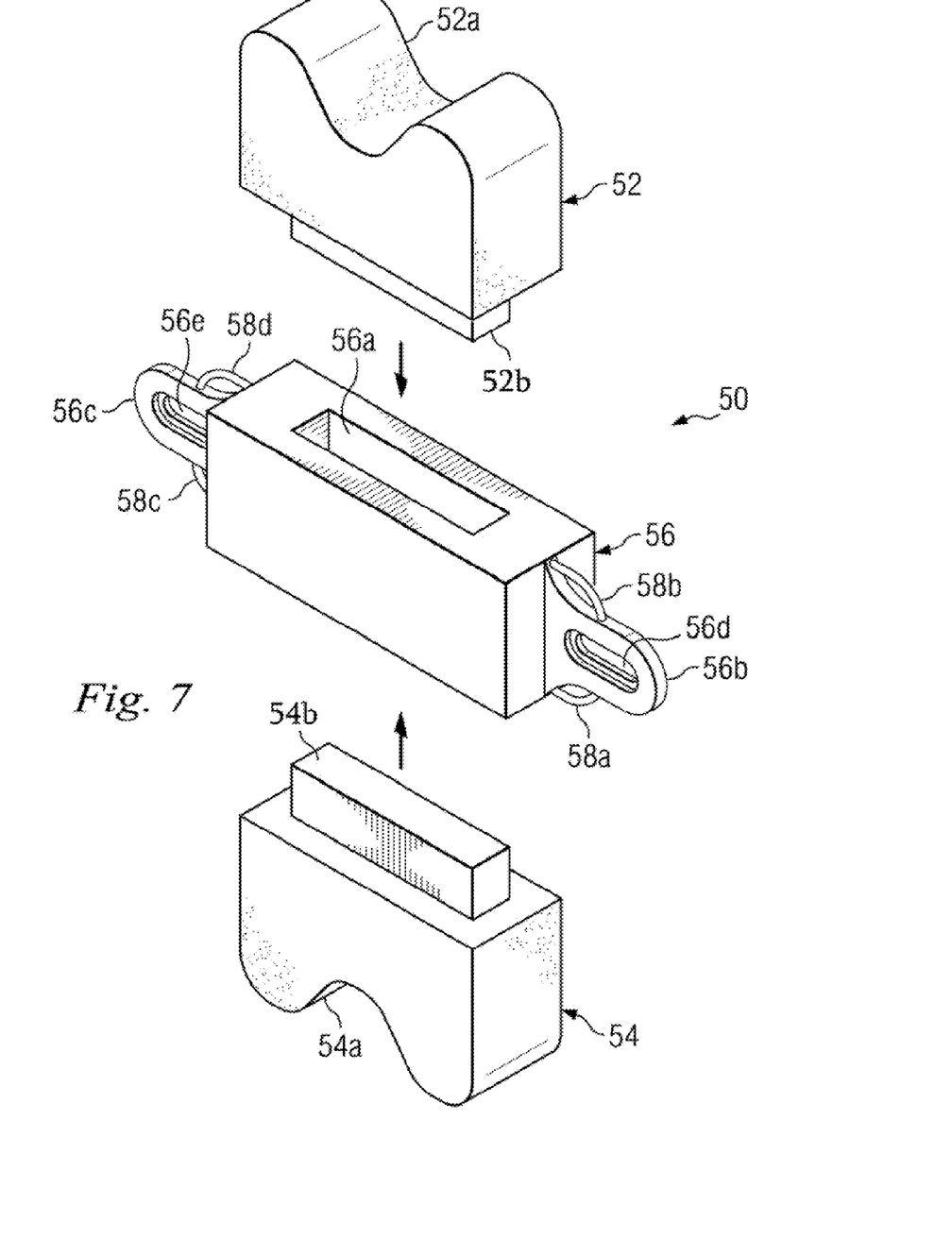
FIG. 7 is an enlarged, isometric, exploded view of an alternate embodiment of the prosthetic device of FIG. 5.

A prosthetic device 50 according to another embodiment is shown in detail in FIG. 7 and includes a spacer 52 which is substantially rectangular in shape with the exception that a curved notch 52a, is formed in one end portion. A tab 52b projects from the other end of the spacer 52 for reasons to be described.

A spacer 54 is also provided which is substantially rectangular in shape with the exception that a curved notch 54a is formed in one end portion and a tab 54b projects from the other end of the spacer 54.

A connector 56 is designed to fit over the tabs 52b and 54b of the spacers 52 and 54, respectively, to connect them. To this end, the connector 56 has a through opening 56a with a cross section slightly greater than the cross sections of the tabs 52b and 54b.

Two tabs 56c and 56b extend out from the respective ends of the connector 56, and elongated openings 56e and 56d extend through the respective tabs for receiving screws, for reasons to be described.

Two protrusions 58a and 58b extend from the sides of the tab 56b and two protrusions 58c and 58d extend from the sides of the tab 56c. The protrusions are for the purpose of receiving tethers, or the like, to tether the device 50 to the vertebrae V4 and/or V5.

To connect the spacers 52 and 54, their respective tabs 52b and 54b are inserted into the opening 56a of the connector 56 from opposite ends of the opening until the corresponding shoulders of the spacers 52 and 54 engage the corresponding ends of the connector 56. The spacers 52 and 54 and the connector are sized so that the tabs 52b and 54b engage the inner wall of the connector 56 in a friction fit so as to retain the spacers 52 and 54 in the connector.

Since the spinous process of the vertebra V4 has been removed, the device 50 is implanted between the spinous process 22 of the vertebra V3 and the spinous process 22 of the vertebra V5. In the implanted position, the spinous process 22 of the vertebra V3 extends in the notch 52a of the spacer 42, and the spinous process 22 of the vertebra V5 extends in the notch 54a. The dimensions of the device 50 are such that, when it is implanted in this manner, the elongated openings 56d and 56e extend over the pedicles 26a and 26b (FIG. 3) of the vertebra V4.

Although not shown in the drawing, tethers can be tied between the protrusions 58a-58d and the vertebrae V3, V4, and/or V5 to provide additional support and resistance.

The spacers 52 and 54 could be fabricated from a relatively soft material, such as soft plastic, including silicone, while the connector 56 could be fabricated from a relatively stiff material, such as hard plastic or rubber. In the latter context, the surgeon could be provided with several connectors 56 that vary in stiffness. Thus, once the surgeon ascertains the condition of the vertebrae V3, V4, and V5 (FIG. 3) and determines the particular stiffness that is needed, the proper connector 56 can be selected.

Thus, when the device 50 is implanted between the spinous processes 22 of the vertebrae V3 and V5 in the manner discussed above, the relatively flexible, soft spacers 52 and 54 provide a non-rigid connection to the vertebrae V3 and V5 that readily conforms to the spinous processes 22 of the vertebrae V3 and V5, and provides excellent shock absorption. Also, the connector 56 adds stiffness, compressive strength and durability, and the screws 49 provide a rigid connection to the vertebra V4.

It is understood that other variations may be made in the foregoing without departing from the invention and examples of some variations are as follows:

Any conventional substance that promotes bone growth, such as HA coating, BMP, or the like, can be incorporated in the prosthetic device of the above embodiments.

One or more of the components of the above devices may have through holes formed therein to improve integration of the bone growth.

The surfaces of the body member defining the notch can be treated, such as by providing teeth, ridges, knurling, etc., to better grip the spinous processes and the adapters.

The body member can be fabricated of a permanently deformable material thus providing a clamping action against the spinous process.

The spacers and associated components of one or more of the above embodiments may vary in shape, size, composition, and physical properties.

Through openings can be provided through one or more components of each of the above prosthetic devices to receive tethers for attaching the devices to a vertebra or to a spinous process.

The prosthetic device of each of the above embodiments can be placed between two vertebrae in the vertebral column 10 other than the ones described above.

The prosthetic device of each of the above embodiments can be fabricated from materials other than those described above.

The relative stiff components described above could be made of a resorbable material so that their stiffness would change over time.

The prosthesis of the above embodiments can be implanted between body portions other than vertebrae.

In the embodiment of FIG. 7, the spacers 52 and 54 can be fabricated from a relatively stiff material and the connector 56 from a relatively soft, flexible material.

The prostheses of the above embodiments can be inserted between two vertebrae following a discectomy in which a disc between the adjacent vertebrae is removed, or a corpectomy in which at least one vertebra is removed.

The spatial references made above, such as "under", "over", "between", "flexible, soft", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A method of implanting a spinal prosthesis comprising:
   inserting a first relatively flexible member between superior and inferior spinous processes associated with respective superior and inferior vertebrae; the superior vertebra and inferior vertebra separated by an intermediate vertebra; the first member having a channel that extends, after insertion, laterally through the first member;
   inserting a second relatively stiff member through the channel such that the second member is operatively connected to the first member;
   removing the second member from the channel and inserting a third relatively stiff member through the channel such that the third member is operatively connected to the first member; wherein the third member has a different stiffness than the second member;
   anchoring the third member to the intermediate vertebra, while inserted through the channel, at first and second locations disposed on respective first and second lateral sides of the intermediate vertebra.

2. The method of claim 1 wherein the first member comprises first and second notches and wherein inserting the first member further comprises engaging the first notch with the superior spinous process and engaging the second notch with the inferior spinous process.

3. The method of claim 1 wherein the third member includes first and second tabs extending from opposite ends thereof and wherein anchoring the third member to the intermediate vertebra comprises connecting tethers to the first and second tabs and tethering the third member to the intermediate vertebra.

4. The method of claim 1 wherein the third member includes first and second tabs extending from opposite ends thereof; wherein said inserting the third member comprises disposing the third member such that the first and second tabs extend over the pedicles of the intermediate vertebra; and wherein anchoring the third member to the intermediate vertebra comprises inserting screws through the first and second tabs such that the screws are driven into the pedicles of the intermediate vertebra.

5. A method of implanting a spinal prosthesis comprising:
   providing a main body member and a plurality of inserts, each having different stiffness from the other; the main body member being more flexible than the inserts;
   inserting the main body member between superior and inferior spinous processes associated with respective superior and inferior vertebrae; the superior vertebra and inferior vertebra separated by an intermediate vertebra; the main body member having, after said inserting:
      an upwardly facing concave notch engaging the superior spinous process;
      a downwardly facing concave notch engaging the inferior spinous process;
      a channel that extends laterally through the main body member;
   selecting one of the inserts based on its relative stiffness;
   coupling the selected insert to the main body by inserting the selected insert through the channel;
   anchoring the selected insert to the intermediate vertebra, while inserted through the channel, at first and second locations disposed on respective first and second lateral sides of the intermediate vertebra.

6. The method of claim 5 wherein the selected insert includes first and second tabs extending from opposite ends thereof and wherein anchoring the selected insert to the intermediate vertebra comprises inserting screws through the tabs and driving the screws into the intermediate vertebra.

7. The method of claim 5 wherein the selected insert includes first and second tabs extending from opposite ends thereof and wherein anchoring the selected insert to the intermediate vertebra comprises connecting tethers to the tabs and tethering the selected insert to the intermediate vertebra.

8. The method of claim 5 wherein the selected insert is a second insert; and, prior to inserting the second insert, the method further comprises inserting a first insert through the channel and thereafter removing the first insert from the channel; wherein the second insert has a different stiffness than the first insert.

9. A method of implanting a spinal prosthesis comprising:
   providing a first body member and a plurality of second body members, each having different stiffness from the other; the first body member being more flexible than the second body members;
   selecting a first of the second body members;
   inserting the first body member between superior and inferior spinous processes associated with respective superior and inferior vertebrae; the superior vertebra and inferior vertebra separated by an intermediate vertebra; the first body member, after said inserting:
      coupled to the first of the second body members; and
      having an upwardly facing concave notch engaging the superior spinous process;
   selecting a second of the second body members based on its relative stiffness;
   decoupling the first of the second body members from the first body member and thereafter engaging the second of the second body members with the first body member;
   thereafter, anchoring the second of the second body members to the intermediate vertebra, while engaged with the first body member and disposed so as to extend through a sagittal plane defined by the first and second vertebrae, at first and second locations disposed on respective first and second lateral sides of the intermediate vertebra.

10. The method of claim 9 wherein the first body member includes a first tab extending downwardly therefrom and wherein engaging the second of the second body members with the first body member comprises inserting the first tab into a recess on a superior side of the second of the second body members.

11. The method of claim 10 further comprising:
engaging the second of the second body members with a third body member; the third body member:
being more flexible than the second body members;
having a downwardly facing concave notch for engaging the inferior spinous process;
having a second upwardly extending tab extending into the second of the second body members;
inserting the second of the second body members between the superior and inferior spinous processes, while engaged with said first and third body members, so the second of the second body members extends through the sagittal plane and the concave notch of the third body member engages the inferior spinous process while the concave notch of the first body member engages the superior spinous process.

12. The method of claim 9 wherein the second of the second body members includes first and second tabs extending from opposite ends thereof; and wherein anchoring the second of the second body members to the intermediate vertebra comprises connecting tethers to the first and second tabs and tethering the second of the second body members to the intermediate vertebra.

13. The method of claim 9:
wherein the second of the second body members includes first and second tabs extending from opposite ends thereof;
further comprising inserting the second of the second body members between the superior and inferior spinous processes, while engaged with the first body member, so the second of the second body members extends through the sagittal plane and the first and second tabs extend over the pedicles of the intermediate vertebra; and
wherein anchoring the second of the second body members to the intermediate vertebra comprises inserting screws through the first and second tabs such that the screws are driven into the pedicles of the intermediate vertebra.

14. The method of claim 9:
wherein inserting the first body member between superior and inferior spinous processes comprises receiving the superior and inferior spinous processes in first and second concave notches on the first body member, respectively;
wherein the decoupling the first of the second body members from the first body member comprises disengaging the first and second concave notches from the superior and inferior spinous processes, respectively, and removing both the first body member and the first of the second body members from between the superior and inferior spinous processes.

* * * * *